United States Patent
Haase et al.

(10) Patent No.: US 11,664,128 B2
(45) Date of Patent: May 30, 2023

(54) ESTIMATING FLOW TO VESSEL BIFURCATIONS FOR SIMULATED HEMODYNAMICS

(71) Applicant: KONINKLIJKE PHILIPS N.V., Eindhoven (NL)

(72) Inventors: Christian Haase, Hamburg (DE); Holger Schmitt, Luetjensee (DE); Michael Grass, Buchholz in der Nordheide (DE); Arjen Van Der Horst, Tilburg (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 435 days.

(21) Appl. No.: 16/647,799

(22) PCT Filed: Sep. 12, 2018

(86) PCT No.: PCT/EP2018/074533
§ 371 (c)(1),
(2) Date: Mar. 16, 2020

(87) PCT Pub. No.: WO2019/053030
PCT Pub. Date: Mar. 21, 2019

(65) Prior Publication Data
US 2020/0265958 A1   Aug. 20, 2020

(30) Foreign Application Priority Data
Sep. 18, 2017   (EP) .................... 17191608

(51) Int. Cl.
*G06T 7/00* (2017.01)
*G16H 50/30* (2018.01)
(Continued)

(52) U.S. Cl.
CPC ............. *G16H 50/30* (2018.01); *G06F 30/28* (2020.01); *G06T 7/0012* (2013.01); *G16H 30/40* (2018.01); *G06T 2207/10081* (2013.01)

(58) Field of Classification Search
CPC ........ G16H 50/30; G16H 30/40; G06F 30/28; G06T 7/0012; G06T 2207/10081
See application file for complete search history.

(56) References Cited

U.S. PATENT DOCUMENTS

| | | | |
|---|---|---|---|
| 2010/0284587 A1* | 11/2010 | Malek | ............... A61B 5/02014 382/128 |
| 2014/0355858 A1 | 12/2014 | O'Dell et al. | |
| 2015/0038860 A1 | 2/2015 | Fonte | |

FOREIGN PATENT DOCUMENTS

| | | |
|---|---|---|
| JP | 2007202957 A | 8/2007 |
| JP | 2016528975 A | 9/2016 |
| WO | 2016001017 A1 | 1/2016 |

OTHER PUBLICATIONS

International Search Report & Written Opinion of PCT/EP2018/074533, dated Dec. 11, 2018.

(Continued)

*Primary Examiner* — Antonio A Caschera (57) ABSTRACT

An apparatus for assessing a patient's vasculature and a corresponding method identify the bifurcations in a vessel of interest on the basis of a local change in at least one geometric parameter value of the vessel of interest and adjust the fluid dynamics inside the vessel of interest to take account for said bifurcations.

15 Claims, 3 Drawing Sheets

(51) Int. Cl.
*G16H 30/40* (2018.01)
*G06F 30/28* (2020.01)

(56) References Cited

OTHER PUBLICATIONS

Berry, Colin et al, "Importance of collateral circulation in coronary heart disease", European Heart Journal, Feb. 2007, vol. 28 No. 3, pp. 278-291; DOI: 10.1093/eurheartj/ehl446.

* cited by examiner

ESTIMATING FLOW TO VESSEL BIFURCATIONS FOR SIMULATED HEMODYNAMICS

CROSS-REFERENCE TO PRIOR APPLICATIONS

This application is the U.S. National Phase application under 35 U.S.C. § 371 of International Application No. PCT/EP2018/074533, filed on Sep. 12, 2018, which claims the benefit of European Patent Application No. 17191608.3, filed on Sep. 18, 2017. These applications are hereby incorporated by reference herein.

FIELD OF THE INVENTION

The present invention relates to an apparatus for assessing a patient's vasculature, a corresponding method and a respective computer program. In particular, the present invention relates to an improved assessment of a vessel of interest in the patient's vasculature using a physiological model derived from one or more diagnostic images to more accurately identify minor vessel branches extending from the vessel of interest.

BACKGROUND OF THE INVENTION

Functional stenosis in coronary arteries is typically evaluated by regarding the hemodynamics, in particular the blood flow rate, through a vessel of interest of the coronary vasculature. Hereby, the grading of the stenosis may particularly be performed using Fractional Flow Reserve (FFR) or Instantaneous Wave-Free Ratio (iFR). Both, FFR as well as iFR, are an indicator for the remaining maximum flow capability in a vessel affected by stenosis. In FFR/iFR measurements, the ratio of the pressure distal the stenosis ($P_d$) to the pressure in the aorta ($P_a$) is used as a surrogate for the respective flow measurements. Hereby, it is assumed that $Q_{stenosis}/Q_{healthy} \approx P_d/P_a$.

FFR measurements have to be performed during maximal blood flow, i.e. under hyperemia, which may cause discomfort in the patient. In contrast, iFR measurements are performed at rest during a specific period in diastole, thereby avoiding the necessity to induce hyperemia in the patient. By foregoing this necessity of hyperemia, the comfort of the patient is greatly improved.

For determination of FFR and/or iFR, a pullback of a pressure wire through a vessel of the patient in which the stenosis is suspected may typically be performed and the pressure for a plurality of intravascular positions along said vessel may be determined.

On the basis of these FFR/iFR measurements, potential treatment options may be considered and the patient may be treated in accordance with one or more of these options. Another important index to determine the best treatment option is the so-called Coronary Flow Reserve (CFR), which defines the maximum increase in blood flow through the vasculature above the normal resting volume. CFR may typically be measured by an intravascular wire that measures blood flow velocities via a Doppler sensor at its tip. The positioning of this sensor is however challenging, which leads to a high risk of performing inaccurate measurements. Also, positron emission tomography (PET) or Doppler echocardiography may be used.

Thus, the measurement of hemodynamic indices such as FFR/iFR and CFR is often performed invasively. In order to reduce the number of invasive procedures on the patient, in recent years efforts have been made to determine hemodynamic indices using a so-called "virtual" approach. In such a virtual approach, the hemodynamic indices are simulated on the basis of a physiological model derived from diagnostic image data of the patient's coronary vasculature (or a part thereof). As an example of such diagnostic image data coronary angiography data is mentioned.

By means of the physiological modeling, an FFR/iFR/CFR value may be estimated and a decision may be made which treatment options are available for the patient. In order to achieve satisfying treatment guidance, hereby, the virtual FFR/iFR/CFR values have to be determined as accurately as possible.

In that respect, WO 2016/001017 discloses an apparatus and a method for improving the accuracy of non-invasive determination of the FFR value based on a representation of the coronary artery system of a patient and respective patient-specific boundary conditions derived from projection data obtained for the patient.

SUMMARY OF THE INVENTION

So far, approaches in improving the accuracy of the modeling of hemodynamic indices have been focused on using patient-specific boundary conditions derived e.g. directly from the diagnostic image data. Using these patient-specific boundary conditions, the fluid dynamics for the vessel of interest may be simulated and the respective hemodynamic indices may be calculated on the basis of these simulations.

These approaches typically neglect the outflow of the blood from the vessel of interest into minor vessel branches. One reason for this is the fact that, in many diagnostic images, these vessel branches may not be visible and/or their connection to the vessel of interest may not be clearly identified. This is particularly true in the case where only a single 2D diagnostic image is used due to vessel overlap and unsuitable angulation. As a result, the size, number and the amount of blood these branches carry may not be determined.

However, the outflow to vessel branches may have a significant influence on the fluid dynamics through the vessel of interest, as the volumetric (blood) flow rate, which is an important factor in the fluid dynamics simulation. Accordingly, in order to more precisely estimate the fluid dynamics, an accurate assessment of the outflow rates to minor vessel branches along the vessel of interest is of great importance.

It is therefore an object of the present invention to provide an improved apparatus and a corresponding method for assessing a patient's vasculature.

It is a further object of the invention to provide an apparatus for assessing a patient's vasculature with high accuracy which allows for a reliable identification of minor vessel branches extending from the main vessels of said vasculature. Even more particularly, it is an object of the present invention to provide an apparatus for assessing and modeling the coronary physiology on the basis of one or more diagnostic images with which important hemodynamic indices, such as FFR, iFR or CFR may be determined with high accuracy.

Therefore, an apparatus for assessing a patient's vasculature is provided. The apparatus comprises an input unit configured to receive at least one diagnostic image of the vasculature, a modeling unit configured to generate, on the basis of the at least one diagnostic image, a physiological model, comprising a geometric model of a vessel of interest in the vasculature and an extraction unit configured to extract, on the basis of the geometric model, a plurality of geometric parameter values for a geometric parameter of the vessel of interest at a plurality of positions along a longitudinal axis of the vessel of interest. The apparatus further comprises an evaluation unit configured to determine, from the plurality of geometric parameter values at the plurality of positions, a local change of at least one geometric parameter value at at least one candidate position and to predict, at the at least one candidate position, a presence of at least one vessel branch of the vessel of interest.

Thus, the apparatus allows to detect vessel branches in the diagnostic image data based on a localized variation of the value of a geometric parameter describing the geometry of the vessel. More particularly, the apparatus is configured to predict the presence of a vessel branch at a candidate position at which the value derived for said geometric parameter exhibits a local variation, in some specific examples, a local reduction.

In this context, the term diagnostic image may particularly refer to an image representing the coronary vasculature of a patient. More particularly, the diagnostic image may represent the coronary vasculature including a vessel of interest. In this context, the term vasculature may refer to a vessel tree or a single vessel. The term vasculature may particularly refer to a vessel segment of the vessel of interest, for which a modeling is performed.

In some embodiments, the diagnostic image may be obtained by a (non-invasive) diagnostic imaging modality, such as computed tomography (CT) or magnetic resonance imaging. In a particular embodiment, a single diagnostic 2D X-ray angiography image may be obtained.

Hereby, the diagnostic imaging modality may particularly be gated. The gated diagnostic imaging modality may typically employ a gated reconstruction, in which the acquisition of the diagnostic images is performed in parallel with acquisition of data providing information over the cardiac cycle, such as electrocardiogram (ECG) or photoplethysmographic (PPG) data. This data may hereby be used to gate the image acquisition and the reconstruction by means of respectively selected phase points of the cardiac cycle.

In some embodiments, a physiological model comprising a geometric model of the vessel of interest may be derived from the at least one diagnostic image to model the patient's vasculature.

In this context, the term physiological model may particularly refer to any kind of model of the coronary vasculature of said patient. To that end, a modeling unit is provided which generates the physiological model from the diagnostic image. In order to do so, the modeling unit may segment the vessel of interest into a plurality of segments. On the basis of this segmentation, the physiological model of the vessel of interest, or a segment thereof, may be generated, which comprises a geometric model of the vessel of interest, i.e. a geometric representation of the vessel of interest. This geometric model may be a two-dimensional model or a three dimensional model.

In some embodiments, the generating of the physiological model comprising the geometric model may merely refer to a deriving of a cross sectional area and/or a vessel diameter of the vessel of interest.

In some embodiments, the generating of the physiological model may further encompass a determination of the fluid dynamics through the vessel of interest. In these embodiments, the physiological model may particularly comprise a fluid dynamics model representing the blood flow through the vessel of interest.

The fluid dynamics model is generated by performing calculations that simulate the interaction of the blood with the vessel wall, i.e. the inner surface of the vessel through which the blood is flowing. These interactions are hereby defined by certain boundary conditions that take account of the properties of the vessel, such as vessel wall composition, vessel wall elasticity and vessel impedance, bifurcations in the vessel as well as blood properties, such as blood viscosity.

When generating the fluid dynamics model, typically, generalized boundary conditions may be used. In this context, the term generalized may refer to the same boundary conditions being used for all patients or to boundary conditions being used for particular patient groups (distinguished by age, gender, physiological condition or the like).

In some embodiments, the fluid dynamics model may be integrated with the geometric model, insofar as it represents the fluid dynamics of the blood at each point of the geometric model.

It shall be understood that the physiological model generated from the diagnostic image data does not include the vessel branches extending from the vessel of interest since these vessel branches, as indicated herein above, may not be clearly identified from the at least one diagnostic image. In that respect, the improved apparatus for assessing the patient's vasculature allows to add these vessel branches into the physiological model, i.e. into the geometric model of the vessel of interest as well as the model describing the fluid dynamics through the vessel of interest.

In order to achieve this, the geometric model comprised in the physiological model may particularly be used to extract a plurality of geometric parameter values at a plurality of positions along the longitudinal axis of the vessel of interest.

In this context, the term geometric parameter may refer to any parameter that is representative of the geometry of the vessel of interest. In some embodiments, the geometric parameter may particularly refer to a vessel diameter, a cross sectional shape, cross sectional area of the vessel or similar geometric measures. The term geometric parameter value may particularly refer to the value of said geometric parameter at a particular position of the vessel of interest.

To that end, it shall further be understood that the plurality of positions along the longitudinal axis of the vessel refers to a plurality of positions as represented by the geometric model, i.e. each of the geometric parameter values is modeled, using the geometric model, at a position of said geometric model that corresponds to a respective position in the vessel of interest that is represented by said model.

Further, the determination of a local change, i.e. a localized variation, of the least one geometric parameter value shall be understood as the evaluation unit regarding the plurality of geometric parameter values as a function of the vessel length (or the length of the vessel segment). That is, each of the geometric parameter values is regarded at its respective position along the longitudinal axis of the vessel of interest.

Hereby, it is determined at which positions the geometric parameter value shows a local change compared to the remaining geometric parameter values. That is, the course of the function representing the geometric parameter value as a function of the vessel length is considered and localized increases and/or decreases and/or local minima or maxima are considered as an indication that a candidate position may be found at this location. To that end, the term candidate position may particularly refer to a position at which a vessel branch may be located.

In some exemplary embodiments, the local change may particularly refer to a localized reduction of the geometric parameter value at that particular position. Hereby, this reduction may correspond to a local minimum of the geometric parameter value and/or to a pronounced decrease of the geometric parameter value.

This prediction of the vessel branches at the candidate positions in the vessel of interest allows to add the vessel branches located at these positions into the physiological model. That is, the prediction of the vessel branches allows to adapt the geometric model to include a geometric representation of the vessel branches extending from the vessel of interest. Further, the prediction allows to adapt the fluid dynamics model to include the outflow of the fluid from the vessel of interest into the calculation of the fluid dynamics through said vessel of interest. Thus, by predicting the vessel branches at the candidate positions, a more accurate assessment of the vasculature with respect to both, geometry as well as hemodynamic parameters may be achieved.

According to an embodiment, the at least one diagnostic image is obtained using X-ray angiography. X-ray angiography is a diagnostic imaging technique particularly well-suited to visualize blood vessels in the (human) body. X-ray angiography is typically performed by injecting a contrast agent into the blood vessels and subsequently irradiating the body part with the contrast agent-filled blood vessels with X-ray radiation to obtain a two-dimensional (2D) diagnostic image in which the contrast agent-filled blood vessels are clearly visible.

The diagnostic image may thus particularly be an X-ray angiography image of the coronary arteries of the patient comprising at least one vessel of interest. More particularly, the at least one diagnostic image from which the physiological model is generated may be a single 2D X-ray angiography image of a vessel of interest. In this case, the physiological model may particularly be a two-dimensional model in which a third dimension is approximated, e.g. by assuming a circular shape of the vessel.

In order to obtain a sufficiently well-resolved physiological model, the X-ray angiography image should hereby have sufficient contrast agent filling. Furthermore, the degree of foreshortening and overlap in the X-ray angiography image should be sufficiently low. This increases the quality of the image and simplifies the generation of the physiological model.

According to yet another embodiment, the physiological model further comprises a lumped parameter fluid dynamics model and the modeling unit is configured to adapt the lumped parameter fluid dynamics model based on the predicting of the at least one vessel branch at the at least one candidate position.

In some embodiments, the physiological model may comprise a lumped parameter fluid dynamics model to simulate the fluid dynamics through the vasculature. More particularly, the lumped parameter fluid dynamics model may be used to simulate the fluid dynamics through the vessel of interest or a segment thereof.

A lumped parameter fluid dynamics model hereby refers to a model in which the fluid dynamics of a vasculature are approximated by a topology of discrete entities. More particularly, in the lumped parameter fluid dynamics model the fluid dynamic resistance in the vessel is approximated by a series of resistors $R_i$, while the termination of a vessel, or a vessel segment, may be approximated by a resistor $R_O$ representing an outlet boundary condition followed by an element representing ground.

These lumped parameter fluid dynamics models reduce the number of dimensions compared to other approaches such as Navier-Stokes or the like. Accordingly, using a lumped parameter fluid dynamics model may allow for a simplified calculation of the fluid dynamics inside the vessels and may ultimately result in reduced processing time.

In some embodiments, the modeling unit may be configured to adapt the lumped parameter fluid dynamics model to take account of the predicted vessel branches, i.e. the vessel outlets through which a part of the fluid flows out of the vessel of interest. In this context, the term adapting may refer to an adjustment of the fluid dynamics model comprised in the physiological model. More particularly, the term adapting may refer to an adjustment to include the effects of the vessel branches on the fluid dynamics in the vessel of interest.

That is, the adapting of the lumped parameter model may encompass an inclusion of the fluid outflow to these vessel branches from the vessel of interest. In other words, the lumped parameter fluid dynamics model allows to adjust the fluid dynamics such as to account for bifurcations occurring in the vessel of interest in case of vessel branches.

In a lumped parameter fluid dynamics model, the outflow to such vessel branches may be modeled by respective resistors $R_{Oi}$, each having a respective outlet resistance. Thus, the adapting of the lumped parameter fluid dynamics model may particularly be performed by including the resistors $R_{Oi}$ to represent the outlet resistances at the candidate positions i. Hereby, the resistors $R_{Oi}$ may only be able to accurately model the fluid dynamics through the respective vessel branches if their respective resistances are correctly estimated.

To that end, the outlet resistances of resistors $R_{Oi}$ at a position i may particularly be defined by the localized outflow rate of the fluid from the vessel of interest. In some embodiments, this localized outflow rate may be determined from the volumetric flow rate, which may be calculated based on the form follows function principle described by Murray's law:

$$Q = k^* D^3.$$

Hereby, Q corresponds to the volumetric flow rate, D is the vessel diameter and k is a proportionality constant. It shall be understood that, although in the exemplary embodiment, Murray's law is used to determine the volumetric flow rate, further, different correlations Q(D) may also be used. More particularly, other correlations Q(D) may be used to describe the relation between volumetric flow rate and vessel diameter for other parts of the vasculature.

In the current example, the geometric parameter value derived from the geometric model may particularly comprise a value for a vessel diameter, a local average vessel diameter or an estimated healthy vessel diameter which virtually removes the effect of disease on the vessel diameter, at a plurality of positions. Hereby, it may be assumed that the volumetric flow rate is reduced by an outflow to a vessel branch.

Thus, it may be assumed that the local outflow rate is represented by the difference between the volumetric flow rate at a first position in the vessel (proximal to the vessel branch) and the volumetric flow rate at a second position (distal to the vessel branch). Since the candidate positions i for the vessel branches have already been predicted, it can hereby by assumed that the local outflow rate may be determined as the difference between the volumetric flow rate at a first candidate position i and the volumetric flow rate at a second candidate position i+1:

$$\Delta Q(i,i+1) = Q_i - Q_{i+1}.$$

In order to determine the volumetric flow rate at a candidate position i, one has to calculate based on Murray's law:

$$Q_i = k^* D_i^3.$$

This gives for the local outflow rate $\Delta Q(i,i+1)$:

$$\Delta Q(i,i+1) = k^*(D_i^3 - D_{i+1}^3).$$

The thus determined local outflow rate may be used to approximate the outlet resistance of resistor $R_{Oi}$ at position i according to $$R_{Oi} = C/\Delta Q(i,i+1) = C/k^*(D_i^3 - D_{i+1}^3),$$

wherein C is a corresponding boundary condition describing the inlet pressure of a healthy patient.

The modeling unit may thus be configured to derive, based on the predicted vessel branches at the predicted candidate positions, the outlet resistance of one or more resistors $R_{Oi}$ representing the outflow at a respective candidate position i in the vessel of interest and include the resistor $R_{Oi}$ into the lumped parameter fluid dynamics model. This allows a more accurate modeling of the fluid dynamics inside the vessel of interest, as the outflows to vessel branches are accounted for.

Further, the modeling unit may also use the magnitude of the calculated localized outflow rate and/or the magnitude of the outlet resistance of the one or more resistors $R_{Oi}$ to estimate the size of a particular vessel branch. More particularly, the modeling unit may estimate that the higher the localized outflow rate—and, accordingly, the lower the respective outlet resistance—the larger the vessel branch. This is particularly true since high localized outflow rates may only occur where the vessel branch is sufficiently large to provide for such an outflow rate. Accordingly, the modeling unit is further configured to derive, from the lumped parameter model, further information about the geometry of the vasculature to be included in the geometric model.

In an even further embodiment, the generating the physiological model comprising the geometric model further includes a segmenting of the vessel of interest into one or more segments. The extraction unit is hereby configured to determine, for each segment, at least one segmented geometric parameter value. Further, the evaluation unit is configured to apply a regression model on the at least one segmented geometric parameter value to calculate, for each segment, an averaged geometric parameter value, and to predict the at least one vessel branch by predicting at least one hemodynamic parameter at the at least one candidate position on the basis of the averaged geometric parameter value of each segment. Alternatively or additionally, the regression model may be applied to calculate, for each segment, an estimated geometric parameter value which represents the patients vasculature at a healthy state without the influence of disease. In this case, the predicting the at least one hemodynamic parameter may be performed on the basis of the estimated geometric parameter value of each segment. In an even further embodiment, the predicting the at least one hemodynamic parameter comprises a predicting of the fluid outflow rate.

In some embodiments, the generating of the physiological model by the modeling unit may comprise a segmentation of the imaged vessel of interest. In this context, the segmenting the diagnostic image of the vessel of interest corresponds to segmenting the vessel of interest represented in the diagnostic image into respective vessel segments. Based on this segmentation, a physiological model comprising a geometric model may be generated representing one or more vessel segments of the vessel of interest.

The extraction unit may then, for each segment of the vessel of interest, extract one or more segmented geometric parameter values at one or more positions in the respective vessel segment. This segmented geometric parameter value is an estimation based on the geometric model included in the physiological model. The generating of the geometric model, in turn, is influenced by the fluid dynamics in the vessel of interest as discussed above. Further, the geometric model may also be influenced by the patient's health status. More particularly, due to lesions at specific locations in the vessel of interest, the vessel may exhibit a different geometry at these locations.

As an example, the segmented geometric parameter may be a segmented vessel diameter. This segmented vessel diameter may be determined for the segments of the vessel of interest based on the geometric model generated from the diagnostic image data. Hereby, the values that may be derived for the segmented vessel diameter at the plurality of positions along the longitudinal axis of the segmented vessel of interest are dependent on the geometry of the vessel of interest, i.e. the vessel of interest may be narrower for some parts of its length and wider for other parts. Further, the segmented vessel diameter is also influenced by the fluid dynamics through the vessel of interest. More particularly, at vessel bifurcations, the vessel diameter may be determined to vary, in particular to be reduced. Furthermore, the vessel diameter may also be reduced due to a local narrowing in the vessel of interest caused e.g. by a stenosis. These factors each influence the vessel diameter derived from the geometric model. Accordingly, the vessel diameter, and, likewise, the other geometric parameter values, should be averaged and/or an estimated vessel diameter should be determined which corresponds to the vessel diameter in the healthy state.

In order to achieve this objective, a regression model is applied on the segmented vessel diameter to predict the average vessel diameter and/or the estimated vessel diameter for each of the plurality of positions. In that context, the regression model particularly refers to a regression analysis by which the relationship between variables may be estimated. In the particular example, the relationship between the volumetric flow rate at a certain vessel location is estimated using the regression model.

Hereby, the regression model may particularly be used to predict the averaged vessel diameter and/or the estimated vessel diameter, i.e. the vessel diameter that would be given if the patient were healthy, at each vessel location. Thus, the average and or estimated vessel diameter is described by the regression model as a function of the position along the longitudinal axis of the vessel of interest. As described above, from this vessel diameter for each position along the vessel it is possible to predict the volumetric flow rate for each position.

In some embodiments, the applying of a regression model particularly refers to performing a combination of a linear and isotonic regression analysis. In some embodiments, the regression analysis further comprises a suppression of diseased segments, which may also lead to a localized reduction in the vessel diameter. That is, diseased segments, as may e.g. be derived from the diagnostic image data, are not regarded for the regression analysis.

By means of the regression model, an averaged geometric parameter value or an estimated geometric parameter value corresponding to a healthy state may be determined for each vessel segment. In some particular embodiments, a plurality of averaged geometric parameter values may be determined for a respective plurality of positions along the longitudinal axis of each vessel segment. In one specific example, an averaged vessel diameter is determined for the plurality of positions in each vessel segment. In other embodiments, a plurality of estimated geometric parameter values corresponding to a healthy state may be determined for the respective plurality of positions along the longitudinal axis of each vessel segment.

In some embodiments, the evaluation unit may particularly determine a localized change of the averaged geometric parameter values. That is, the evaluation unit regards the averaged geometric parameter values as a function of the vessel length (or the length of the vessel segment) and determines the candidate positions i at which the averaged geometric parameter values show a localized variation.

The evaluation unit may further, based on the averaged geometric parameter values determined at the respective candidate positions i, predict at least one hemodynamic parameter value.

In accordance with one example, the averaged geometric parameter value may comprise the averaged vessel diameter. In particular, the evaluation unit may, based on an averaged vessel diameter $D_i$ at a candidate position i, predict the volumetric flow rate $Q_i$ at that particular position as described herein above. In some embodiments, the evaluation unit may particularly use the predicted volumetric flow rate to determine the outflow from the vessel of interest between two candidate positions according to the above-mentioned relation $$\Delta Q(i,i+1)=k*(D_i^3-D_{i+1}^3).$$

Using this predicted local outflow rate, the evaluation unit may identify the parts of the vessel segments at which a high outflow rate may be expected. The evaluation unit may then provide this information to the modeling unit.

The modeling unit may then adapt the physiological model accordingly. In some embodiments, the modeling unit may use the thus identified part of the vessel segments to adjust the physiological model to include the vessel branches. More particularly, the modeling unit may use the information about the vessel segments at which a high outflow rate may be expected to determine, from the diagnostic image data, which vessel branches may be provided at the positions of the high outflow rate.

The modeling unit may adapt the physiological model to simulate the geometry of the vessel branches and/or the fluid dynamics of the corresponding bifurcations in the vessel of interest. That is, the physiological model may be adapted to include the effects of the fluid outflow to the identified vessel branches.

Thus, by means of this virtual outflow approach, the accuracy of the physiological model with respect to the simulation of hemodynamic parameters, such as blood pressure, blood flow, blood viscosity or the like may be improved.

According to yet another embodiment, the evaluation unit is configured to define a region of interest in the at least one diagnostic image on the basis of the at least one candidate position and to output an indication of said region of interest. In yet another embodiment, the evaluation unit outputs the indication of said region of interest to the modeling unit and the modeling unit is configured to adapt the physiological the model using the indication of said region of interest.

In some embodiments, the evaluation unit may further derive, based on the predicted candidate positions, respective regions of interest for the at least one diagnostic image, in which a vessel branch may be found. In some embodiments, the evaluation unit may hereby derive these regions of interest based on the modeling of the local outflow rate at a particular candidate position. Accordingly, the evaluation unit may predict that for a high local outflow rate at a particular candidate position a respective vessel branch may be present. The evaluation unit may then, based on this information, define a region of interest. In some embodiments, the evaluation unit may hereby consider the magnitude of the local outflow rate to estimate the size of the vessel branch and may adjust the region of interest accordingly. In other embodiments, the region of interest may be defined as an area of pre-defined size around a respective candidate position.

The evaluation unit may then output an indication of the region of interest to the display unit and/or the modeling unit. In some embodiments, the indication comprises an information about the location of the region of interest inside the diagnostic image. Further, the indication may comprise an information about the size and/or shape of the region of interest.

In some embodiments, the modeling unit receives the indication from the evaluation unit and identifies, based on the indication, the region of interest in the at least one diagnostic image. Thus, the modeling unit obtains information about the location in the diagnostic image at which the modeling unit should check for potential vessel branches. Using this information, the modeling unit may identify these vessel branches from the diagnostic image. The modeling unit may then use respective information about the vessel branches it may derive from diagnostic image data as an input to the physiological model. Examples for such information may be the diameter and/or length of the vessel branch and/or the course of the vessel branch or the like. The modeling unit may then adapt the physiological model accordingly, as described herein above.

According to a further embodiment, the apparatus comprises a display unit. The evaluation unit hereby outputs the indication of said region of interest to the display unit. The display unit is configured to generate a first graphical representation of the at least one diagnostic image and a second graphical representation of the indication of the region of interest in the diagnostic image data and to jointly display the first graphical representation and the second graphical representation.

A display unit may be any unit capable of displaying a graphical representation of the data, such as a computer screen, a TV screen or the like. The display unit may further comprise a processing unit to generate a graphical representation of the at least one diagnostic image as well as a graphical representation of the indication of the region of interest. More particularly, the display unit may be configured to generate a joint graphical representation, in which the indication of the at least one region of interest is represented as an element of the at least one diagnostic image. To that end, the indication may be represented by an indicator capable of accurately indicating the region of interest. In that respect, the indication may particularly be represented as a circumferential line surrounding the region of interest or a hatched area, covering the region of interest or the like. Alternatively or additionally, the indication may also be represented by an arrow indicating the region of interest, e.g. combined with a colored highlighting of the region.

The generating of the first and second graphical representation may particularly comprise a generating of the first graphical representation of the at least one diagnostic image, a generating of the second graphical representation of the indication and a subsequent integration of the second graphical representation into the first graphical representation a location of the first graphical representation that corresponds to the location of the region of interest in the diagnostic image.

In an even further embodiment, the input unit is configured to receive intravascular measurement data and the evaluation unit is configured to predict, based on the physiological model and the intravascular measurement data, one or more hemodynamic index values at the plurality of positions along the longitudinal axis of the vessel of interest. In one embodiment, the intravascular measurement data comprises at least one pressure gradient acquired in-situ for the vessel of interest. According to yet another embodiment, the one or more hemodynamic index values predicted at the plurality of positions along the longitudinal axis of the vessel of interest comprise at least one of a volumetric flow rate and/or a blood flow velocity.

Hereby, the term intravascular measurement data particularly refers to data that has been acquired in-situ, i.e. from inside a vessel of interest in the patient's vasculature. More particularly, the term intravascular measurement data may refer to an intravascular measurement of one or more hemodynamic parameters inside the vessel of interest. These measurements may typically be performed by introducing a catheter including a measurement device into the vessel of interest and using the measurement device to collect one or more hemodynamic parameter values for the respective hemodynamic parameter to be regarded.

The intravascular measurement data may be received by the input unit and then provided to the evaluation unit. In some embodiments, the input unit particularly receives at least one measured hemodynamic parameter value comprised in the intravascular image data and provides the at least one measured hemodynamic parameter value to the evaluation unit. The evaluation unit then uses the at least one measured hemodynamic parameter value as a further input to the physiological model to derive one or more hemodynamic index values.

In this context, the term hemodynamic index value may particularly refer to the values of hemodynamic parameters that are used to derive diagnostic indices such as Fractional Flow Reserve (FFR), instantaneous wave-Free Ratio (iFR) and/or Coronary Flow Reserve (CFR). Thus, the hemodynamic index value may particularly relate to a volumetric flow rate, a blood flow velocity, a blood pressure or like values.

According to one illustrative example, the intravascular measurement data relates to a measurement of the pressure gradient that has been performed using a respective pressure wire introduced into the vessel of interest. Thus, in this example, the at least one hemodynamic parameter value relates to the pressure gradient $\Delta p = p_o - p_a$ in the vessel of interest. Further, the physiological model has been used to determine the volumetric flow rate $Q_i$ in the vessel of interest at a plurality of candidate positions i. That is, a specific volumetric flow rate $Q_i$ has been determined for each candidate position i, whereby the outflow through respective vessel branches has been taken into account in this determination.

Accordingly, since the outflow from the vessel of interest through particular vessel branches along the length of the vessel (or the vessel segment) has been considered when calculating $Q_i$, $Q_i$ will be different for the different positions along the length of the vessel. Thus, contrary to prior art approaches, the volumetric flow rate along the length of the vessel is not constant anymore, but varies according to the outflow from the vessel of interest.

Taking into account the changes in the volumetric flow rate due to outflows through minor vessel branches, allows to accurately determine, based on the (position-dependent) volumetric flow rate $Q_i$ and the pressure gradient $\Delta p$ the hemodynamic indices needed for accurate differential diagnosis of the patient.

In a further illustrative embodiment, the hemodynamic index to be determined is related to the Coronary Flow Reserve (CFR). CFR is defined as the ratio of the volumetric flow rate under hyperemia to the volumetric flow rate in the resting state:

$$CFR = Q_{hyperemia}/Q_{rest}$$

The CFR value may hereby be determined for various locations along the vessel of interest. Hereby, since the local outflows through minor vessel branches are accounted for, the volumetric flow rate at each location may be different, and, accordingly, the resulting CFR value may vary location-dependently. This is a significant improvement to prior art approaches in which the volumetric flow rate has been assumed to be constant along the vessel of interest, thereby resulting in a likewise constant CFR value along the vessel of interest, which is a clinically unrealistic result.

In some embodiments, the physiological model comprises a lumped parameter fluid dynamics model to calculate the fluid dynamics through the vessel of interest. Upon identification of the vessel branches using the virtual outflow approach, the physiological model comprising the lumped parameter fluid dynamics model may be adapted as described herein above. The adapted physiological model may then be used to calculate a plurality of CFR values along the longitudinal axis of the vessel of interest.

More particularly, the physiological model comprising the lumped parameter fluid dynamics model receives the pressure gradient $\Delta p$ as a further input for simulating the CFR. Using the adapted physiological model and the invasively obtained pressure gradient, the flow rate through the vessel of interest may be calculated using $$\Delta p = \Sigma_i Q_i R_i + Q_i^2 V_i,$$

where $\Delta p$ is the pressure gradient, $Q_i$ is the flow rate at candidate position i, $R_i$ is the linear resistance at candidate position i and $V_i$ is the quadratic resistance at that position.

Hereby, $Q_i$ and $p_i$ at candidate position i are defined as $$Q_i = Q_{i-1} - p_i/R_{Oi}, \text{ and}$$

$$p_i = p_o - \Sigma_{k<i} Q_k R_k + Q_k^2 V_k.$$

On the basis of these relations a plurality of CFR values may be calculated for the plurality of candidate positions i.

Since the simulation of the volumetric flow rate in the lumped parameter fluid dynamics model takes into account the outflow to minor vessel branches, the value of the volumetric flow rate $Q_i$ varies along the positions i. This variation in volumetric flow rate corresponds to a more accurate simulation of the actual flow dynamics in a vessel of interest. Furthermore, it allows to calculate a position-dependent CFR value. Thus, this approach allows to obtain a clinically realistic result for the CFR values from simulations on the basis of a physiological model.

This avoids the necessity of introducing a further catheter into the vessel of interest to determine the CFR value by means of an intravascular flow measurement. Thus, by means of this virtual outflow approach, the simulation of hemodynamic indices may be made more accurate.

In some embodiments, the intravascular measurement data may alternatively or additionally comprise the volumetric flow rate and/or at least one vessel diameter that has been obtained invasively at a particular intravascular position inside the vessel of interest. In one particular embodiment, both the volumetric flow rate and the vessel diameter are determined. In this case, the relation Q(D) may be used as a patient-specific input to calibrate the proportionality constant k according to $$k=Q/D^3$$

Such a calibration of proportionality constant k may further improve the accuracy of the modeled predictions.

In further embodiments, the outflow to minor vessel branches may also be improved using intravascular flow measurements by obtaining the flow-based measurement values while the vessel of interest is occluded distal the flow measurement side. An occlusion of the vessel of interest at a distal position means that the entire flow inside the vessel of interest that has been measured proximal to the occlusion flows into the vessel branches. Thus, this allows to more accurately determine, specifically for each patient, the different outflow rates to the vessel branches. This may further improve the accuracy of the modeled predictions.

According to a further aspect, a method for assessing a patient's vasculature is provided. The method comprises the steps of receiving at least one diagnostic image of the vasculature, generating, on the basis of the at least one diagnostic image, a physiological model comprising a geometric model of a vessel of interest in the vasculature and extracting, on the basis of the geometric model, a plurality of geometric parameter values for a geometric parameter of the vessel of interest at a plurality of positions along a longitudinal axis of the vessel of interest. Further, the method comprises the steps of determining, from the plurality of geometric parameter values at the plurality of positions, a local reduction of at least one geometric parameter value at at least one candidate position, and predicting, at the at least one candidate position, at least one vessel branch of the vessel of interest.

In some embodiments, the method further comprises the steps of segmenting the vessel of interest into one or more segments and determining, for each segment, at least one segmented geometric parameter value. The method further comprises the steps of applying a regression model on the at least one segmented geometric parameter value to calculate, for each segment, an averaged geometric parameter value and predicting the at least one vessel branch by predicting at least one hemodynamic parameter at the at least one candidate position on the basis of the averaged geometric parameter value of each segment.

In a further aspect, a computer program for controlling an apparatus according to the invention is provided, which, when executed by a processing unit, is adapted to perform the method steps according to the invention. In an even further aspect, a computer-readable medium is provided having stored thereon the above-cited computer program.

It shall be understood that the apparatus of claim 1, the method of claim 12, the computer program of claim 14 and the computer-readable medium of claim 15 have similar and/or identical preferred embodiments, in particular as defined in the dependent claims.

It shall be understood that a preferred embodiment of the present invention can also be any combination of the dependent claims or above embodiments with the respective independent claim.

These and other aspects of the invention will be apparent from and elucidated with reference to the embodiments described hereinafter.

DETAILED DESCRIPTION OF EMBODIMENTS

The illustration in the drawings is schematically. In different drawings, similar or identical elements are provided with the same reference numerals.

Figure 1:
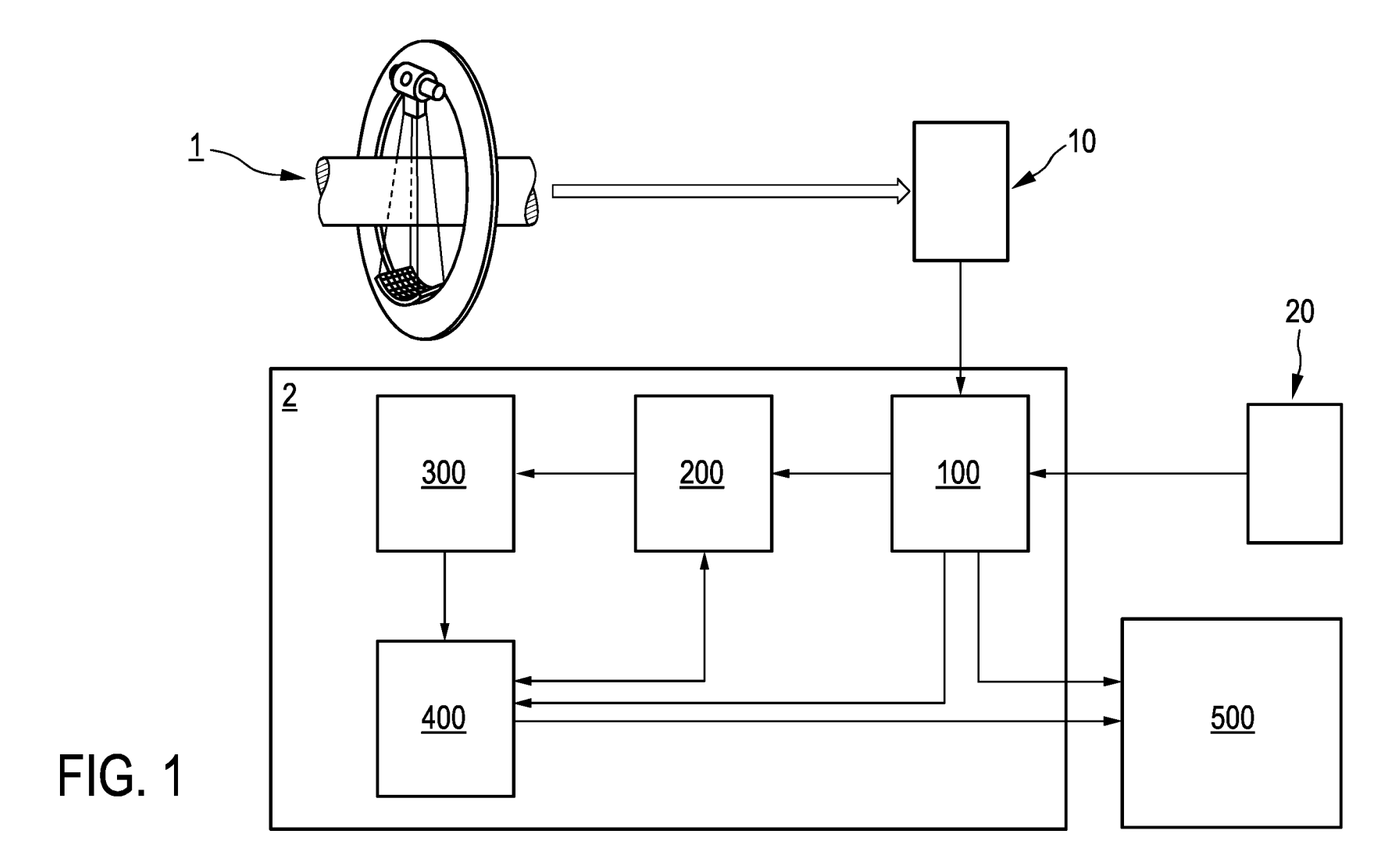
FIG. 1 schematically illustrates an apparatus for assessing a patient's vasculature according to an embodiment.

FIG. 1 represents schematically an exemplary embodiment of an apparatus 2 for assessing a patient's vasculature. The apparatus 2 comprises an input unit 100, a modeling unit 200, an extraction unit 300, an evaluation unit 400 and a display unit 500.

An X-ray system 1, which may for example be a C-arm system, is used to acquire X-ray angiography projection data comprising one or more diagnostic images. Thus, in the exemplary embodiment according to FIG. 1, the at least one diagnostic image 10 is a single two-dimensional (2D) X-ray angiography image.

Input unit 100 of apparatus 2 is configured to receive the single X-ray angiography image 10 from X-ray system 1. Further, input unit 100 is configured to receive, from an intravascular measurement modality, intravascular measurement data 20. In the exemplary embodiment according to FIG. 1, intravascular measurement data 20 has been obtained by introducing a pressure wire into the vessel of interest in the patient's vasculature and measuring a respective pressure gradient Δp inside the vessel of interest.

The input unit 100 provides the X-ray angiography image 10 to modeling unit 200. Modeling unit 200 is configured to receive the X-ray angiography image 10 and to perform a vessel segmentation of the vessel of interest in the vasculature imaged in the X-ray angiography image 10 to generate a physiological model comprising a geometric model of the vessel of interest.

In the exemplary embodiment according to FIG. 1, the generating of the physiological model comprising the geometric model on the basis of the X-ray angiography image 10 particularly includes a modeling of the vessel diameter of the vessel of interest for a plurality of positions along a (simulated) longitudinal axis of said vessel, i.e. along the vessel length. That is, for each segment of the segmented vessel, at least one vessel diameter is derived. Modeling unit 200 then provides the physiological model including at least the at least one vessel diameter to extraction unit 300.

Extraction unit 300 is configured to use the geometric model included in the physiological model to extract a plurality of geometric parameter values for the vessel of interest. In the exemplary embodiment according to FIG. 1, extraction unit 300 extracts a plurality of values for the vessel diameter of the vessel of interest at the plurality of positions. Since the vessel of interest has been segmented, this encompasses an extraction of a plurality of values for the vessel diameter for each of the segments of the vessel. Accordingly, in the exemplary embodiment, extraction unit 300 extracts multiple segmented vessel diameter values.

Extraction unit 300 then provides the extracted values along with the respective position for which they have been extracted to evaluation unit 400.

Evaluation unit 400 receives the X-ray angiography image 10 and the extracted values along with their respective positions. Evaluation unit 400 then calculates, for each of the position, a local average vessel diameter from the extracted values. In this exemplary embodiment, evaluation unit 400 applies a combination of a linear and an isotonic regression to the extracted values to calculate the local average vessel diameter $D_i$ for each position i. Hereby, extraction unit 400 optionally uses a monotonic decrease as an additional condition for the calculation.

Evaluation unit 400 then regards the thus calculated local average vessel diameters $D_i$ as a function of their respective positions i and identifies the candidate positions i, for which the average vessel diameter $D_i$ shows a localized decrease. Evaluation unit 400 then predicts, based on the localized decrease at least one hemodynamic parameter at each of the candidate positions i. In the particular embodiment according to FIG. 1, evaluation unit particularly predicts a fluid outflow rate for each of the candidate positions i.

In the exemplary embodiment of FIG. 1, evaluation unit 400 then regards the predicted fluid outflow rate at each of the candidate positions i and determines, for the subset of candidate positions i for which the predicted fluid outflow rate is high, i.e. is above a pre-defined threshold value, that a minor vessel branch may be branching from the vessel of interest at that particular candidate position i.

To that end, evaluation unit 400 uses the predicted fluid outflow rate to determine, for the X-ray angiography image 10, a region of interest in the proximity of the position in the X-ray angiography image 10 that corresponds to the particular candidate position i in the vessel of interest. That is, evaluation unit 400 determines a region of interest in X-ray angiography image 10 that may potentially include a vessel branch.

According to the example of FIG. 1, evaluation unit 400 then outputs an indicator for the at least one region of interest in the X-ray angiography image 10 to modeling unit 200 and display unit 500. Further, evaluation unit 400 provides the information about the predicted fluid outflow rate at each of the candidate positions i to modeling unit 200.

Modeling unit 200 then adapts the physiological model to include the potential vessel branches at candidate positions i, for which the predicted fluid outflow rate has been high. More particularly, modeling unit 200 uses the X-ray angiography image and the indication about the at least one region of interest to identify the vessel branches in the X-ray angiography image, by determining a corresponding vessel branch in the respective region of interest. On the basis of this identification, modeling unit 200 then adapts the geometric model of the vessel of interest to include these vessel branches.

Hereby, modeling unit 200 takes into account the magnitude of the predicted fluid outflow rate at each of the candidate positions i to more accurately estimate the size of each of the vessel branches. That is, modeling unit 200 estimates that higher outflow rates indicate a larger vessel branch and lower outflow rates indicate a smaller vessel branch.

Further, modeling unit 200 adapts the fluid dynamics through the vessel of interest such as to include the bifurcation at each of the candidate positions i, i.e. to take into account the fluid outflow from the vessel of interest at candidate positions i.

In the exemplary embodiment according to FIG. 1, modeling unit 200 subsequently provides the adapted physiological model to evaluation unit 400. Evaluation unit 400 then uses the adapted physiological model and the intravascular measurement data received from input unit 100 to predict a plurality of hemodynamic index values for the plurality of positions in the vessel of interest.

In the particular embodiment according to FIG. 1, the Coronary Flow Reserve ($CFR=Q_{hyperemia}/Q_{rest}$) may be estimated for the plurality of positions along the length of the vessel without the necessity to introduce a further intravascular measurement device capable of measuring blood flow into the vessel. Optionally, evaluation unit 400 provides the information about the CFR values along the longitudinal axis of the vessel of interest to display unit 500.

Display unit 500 receives X-ray angiography image 10 from input unit 100. Further, display unit 500 receives the indication for the at least one region of interest in the X-ray angiography image 10 and, optionally, information about the CFR values derived for the plurality of positions along the longitudinal axis of the vessel of interest.

Display unit 500 then generates a first graphical representation of the X-ray angiography image 10. Further, display unit 500 generates a second graphical representation of the indication of the region of interest. Optionally, display unit may also generate a third graphical representation of the CFR values. Display unit 500 then jointly displays the first graphical representation and the second graphical representation, optionally along with the third graphical representation.

In the exemplary embodiment according to FIG. 1, display unit 500 particularly generates a respective circumferential line as a graphical representation for each region of interest and inserts the respective circumferential line into the graphical representation of the X-ray angiography image 10 at the respective position of the region of interest in the image. That is the circumferential line represents the border of the respective region of interest.

Optionally, the display unit 500 may further generate a graphical representation of a plurality of CFR values along the length of the vessel of interest. Hereby, the graphical representation may particularly include the value of the CFR value and a respective arrow indicating the position for which this value has been predicted.

The display unit 500 may then display the graphical representations. This allows a user, in particular a physician, to gain a more thorough understanding of the patient's vasculature while minimizing the amount of invasive procedures needed for assessment.

Figure 2A:
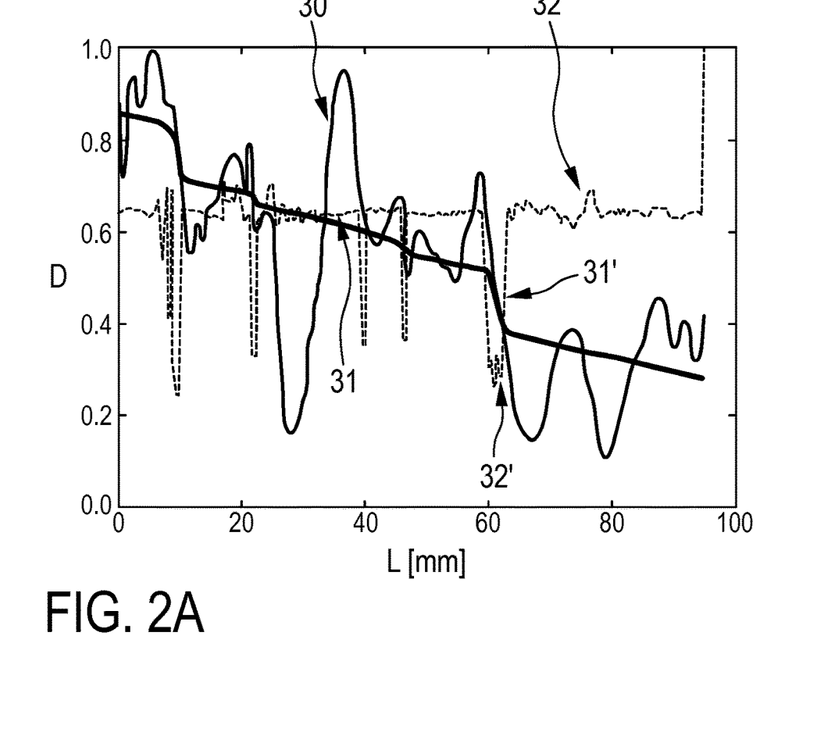
FIG. 2A represents a plot of the segmented and averaged vessel size as well as the calculated outlet resistance as a function of the vessel length according to an embodiment.

In that respect, FIG. 2A schematically illustrates a plot 30 of the extracted vessel diameter and a plot 31 of the averaged vessel diameter $D_i$, respectively (D in arbitrary units) as a function of the length of the vessel of interest (L in mm). In accordance with the exemplary embodiment according to FIG. 2A, the information that may be derived from the plots 30 and 31 may be used to adapt the physiological model used for predicting the hemodynamic index values.

Figure 2B:
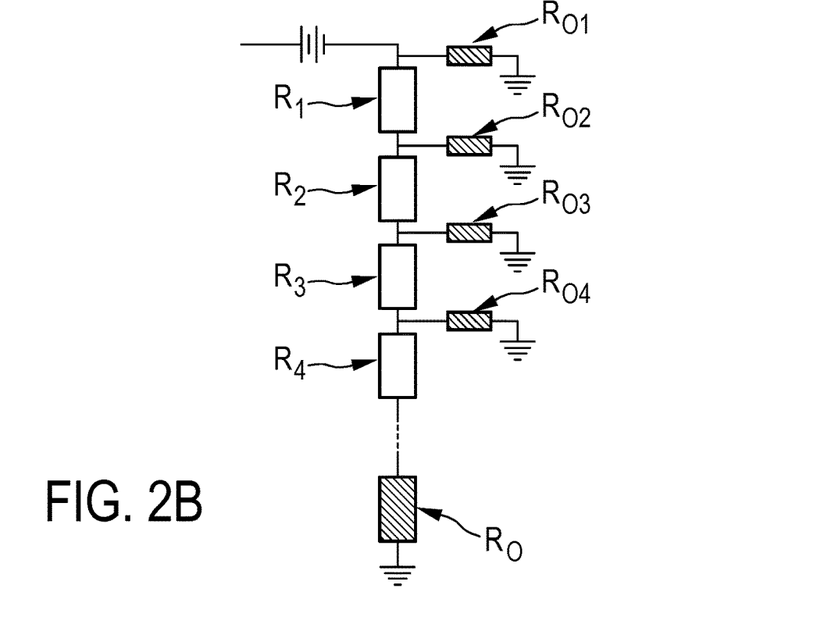
FIG. 2B schematically illustrates the integration of the fluid outflow into a lumped parameter fluid dynamics model according to an embodiment.

In the embodiment according to FIG. 2A, it is assumed that the physiological model comprises a lumped parameter fluid dynamics model to simulate the fluid dynamics through the patients vasculature. FIG. 2B shows an exemplary embodiment of such a lumped parameter fluid dynamics model in which a segment of the vessel of interest is modeled by resistors $R_1$, $R_2$, $R_3$ and $R_4$. The vessel branches, i.e. the locations of fluid outflow from the vessel of interest, are modelled by resistors $R_{O1}$ to $R_{O4}$. Further, the resistor $R_O$ is used to define an outlet boundary condition at the end of the segment of the vessel of interest. In order to adapt the lumped parameter fluid dynamics model to correctly model the fluid outflow from the vessel of interest, the outlet resistance of the resistors $R_{O1}$ to $R_{O4}$ has to be determined. Hereby, the outflow rate for the vessel branches may particularly be determined using a regression model on the extracted vessel diameter to determine an average vessel diameter at the positions of the vessel segment, along with Murray's law to define the relation between the flow rate and the (average) vessel diameter.

More particularly, by applying the regression model on the extracted vessel diameter, the averaged vessel diameter $D_i$ for each candidate position i may be determined. Next, the local outflow rate between two candidate positions i may be determined as the difference between the volumetric flow rate $Q_i$ at candidate position i and $Q_{i+1}$ at the follow-up candidate position i+1:

$$\Delta Q(i,i+1) = k^*(D_i^3 - D_{i+1}^3).$$

As indicated herein above, the magnitude given by this local outflow rate may be used by the modeling unit 200 to determine the size of the vessel branches.

Further, the local outflow rate may be used to approximate the outlet resistance of resistors $R_{Oi}$ according to $$R_{Oi} = C/\Delta Q(i,i+1) = C/k^*(D_i^3 - D_{i+1}^3),$$

wherein C is a corresponding boundary condition describing the inlet pressure of a healthy patient.

In that regard, FIG. 2A shows a plot 32 of the outlet resistances determined for a plurality of positions along the length of the vessel. As may be appreciated from plot 31 in FIG. 2A, the average vessel diameter $D_i$ decreases significantly at position 31'. Accordingly, the outflow rate is rather high and the corresponding outlet resistance at position 32' is low. Since a low outlet resistance corresponds to a high outflow rate, a low outlet resistance may typically be used to represent a large vessel branch.

Thus, the lumped parameter fluid dynamics model may be adapted by selecting the resistances of resistors $R_{Oi}$ in accordance with the calculated outflow rates as described above. Subsequently, the thus adapted physiological model comprising the lumped parameter fluid dynamics model may be used to determine a plurality of hemodynamic index values.

To that end, the physiological model comprising the lumped parameter fluid dynamics model receives intravascular measurement data as a further input. In the exemplary embodiment described herein, the intravascular measurement data comprises a measurement of the pressure gradient $\Delta p = p_o - p_a$ obtained in-situ from the vessel of interest. Using the adapted physiological model and the invasively obtained pressure gradient, the flow rate through the vessel of interest may be calculated using $$\Delta p = \Sigma_i Q_i R_i + Q_i^2 V_i,$$

where $\Delta p$ is the pressure gradient, $Q_i$ is the flow rate at candidate position i, $R_i$ is the resistance at candidate position i and $V_i$ is the volume at that position. Hereby, $Q_i$ and $p_i$ at candidate position i are defined as $$Q_i = Q_{i-1} - p_i/R_{Oi} \text{ and } p_i = p_0 - \Sigma_{k<i} Q_k R_k + Q_k^2 V_k.$$

Using the above relations the value for a flow-related hemodynamic index, such as the CFR, may be calculated from intravascular pressure-based measurements. This avoids the necessity of introducing a further catheter for flow-based measurements, thereby greatly improving the comfort of the patient.

Figure 3:
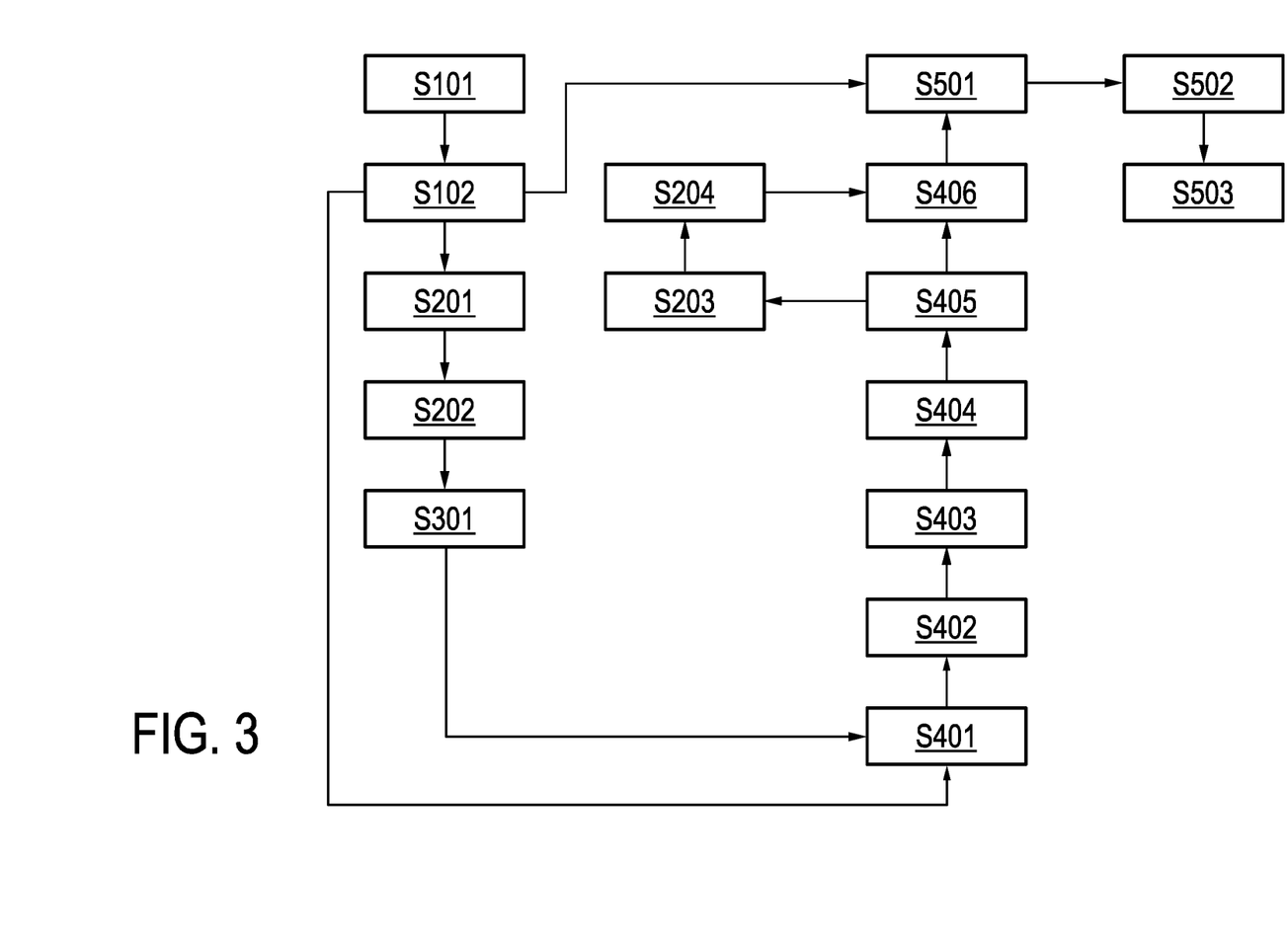
FIG. 3 represents a flow chart for a method for assessing a patient's vasculature according to an embodiment.

FIG. 3 schematically represents a flow chart for a method for assessing a patient's vasculature according to an embodiment. In step S101, input unit 100 receives a single 2D X-ray angiography image 10 from X-ray system 1 and intravascular measurement data 20 from an intravascular measurement modality. In step S102, input unit 100 provides the X-ray angiography image 10 to modeling unit 200 and display unit 500. Further, input unit 100 provides the intravascular measurement data to evaluation unit 400.

In step S201, modeling unit 200 receives the X-ray angiography image 10. In step S202, modeling unit 200 segments the imaged vessel of interest and generates, on the basis of this segmentation, a physiological model comprising a geometric model of the vessel of interest. Modeling unit 200 then provides the physiological model to extraction unit 300.

In step S301, extraction unit 300 receives the physiological model and extracts, on the basis of the geometric model in said physiological model, a plurality of geometric parameter values for the vessel of interest. In the exemplary embodiment according to FIG. 3, the extraction unit 300 extracts a plurality of segmented vessel diameter values as the geometric parameter values and provides the extracted segmented values along with the respective position for which they have been extracted to evaluation unit 400.

In step, S401, evaluation unit 400 receives the X-ray angiography image 10 and the extracted values along with their respective positions from extraction unit 300. Further, evaluation unit 400 receives the intravascular measurement data from input unit 100.

In step S402, evaluation unit 400 calculates, for each of the position, a local average vessel diameter from the extracted values. According to the example of FIG. 3, this calculation is particularly performed by applying a combination of a linear and an isotonic regression to the segmented diameter values to calculate the local average vessel diameter $D_i$ for each candidate position i. Optionally, extraction unit 400 may use the additional condition of monotonic decrease during the calculation.

In step S403, evaluation unit 400 then identifies the candidate positions i, for which the average vessel diameter $D_i$ shows a localized decrease as described herein above and predicts, based on the localized decrease at least one hemodynamic parameter at each of the candidate positions i. In the exemplary embodiment of FIG. 3, this hemodynamic parameter may particularly comprise the outflow rate for each of the candidate positions i.

In step S404, evaluation unit 400 then determines, on the basis of the predicted outflow rate, the subset of candidate positions i for which the predicted outflow rate is high. Based on this, the evaluation unit predicts that at the candidate position i, a vessel branch of the vessel of interest may be found and uses this prediction to define, for the X-ray angiography image 10, a region of interest around the position in the image that corresponds to the particular candidate position i in the vessel of interest.

In step S405, outputs an indicator for the at least one region of interest in the X-ray angiography image 10 to modeling unit 200 and display unit 500. Further, evaluation unit 400 provides the information about the predicted outflow rate at each of the candidate positions i to modeling unit 200.

In step S203, modeling unit 200 adapts the physiological model to include the vessel branches at candidate positions i both, in terms of geometry and fluid dynamics. Hereby, modeling unit 200 uses the X-ray angiography image and the indication about the at least one region of interest to identify the vessel branches in the X-ray angiography image, and adapts the physiological model to include these vessel branches. Hereby, the modeling unit 200 assumes that the size of the vessel branch is larger when the outflow rate determined is higher and smaller, when the respective outflow rate is lower. Subsequently, in step S204, the modeling unit 200 provides the adapted physiological model back to evaluation unit 400.

Evaluation unit 400 then uses, in step S406 the adapted physiological model and the intravascular measurement data to predict a plurality of hemodynamic index values for the plurality of positions in the vessel of interest. In the exemplary embodiment according to FIG. 3, evaluation unit 400 particularly determines a plurality of CFR values for a respective plurality of positions along the vessel of interest and provides the information about the CFR values along the longitudinal axis of the vessel of interest to display unit 500.

In step S501, display unit 500 receives X-ray angiography image 10 from input unit 100. Further, display unit 500 receives the indication for the at least one region of interest in the X-ray angiography image 10. In the exemplary embodiment according to FIG. 3, display unit 500 further receives information about the CFR values derived for the plurality of positions along the longitudinal axis of the vessel of interest.

In step S502, display unit 500 generates a first graphical representation of the X-ray angiography image 10 and a second graphical representation of the indication of the region of interest. In this exemplary embodiment, display unit 500 further generates a third graphical representation of the CFR values. In step S503, display unit jointly displays the first, the second and the third graphical representation. Hereby, the first, second and third graphical representation may particularly embodied as described in relation to FIG. 1.

Although in above described embodiments, the diagnostic images have been obtained using X-ray angiography, it shall be understood that in other embodiments, the diagnostic images may be retrieved by other imaging methods, such as helical computed tomography or sequential computed tomography, magnetic resonance imaging, ultrasound imaging, or the like.

Further, while in the above embodiments, the modeling has been performed on the coronary physiology, in other embodiments, the modeling may likewise be performed on other image-derived physiologies of the human body. As an example, the approach may be applied to model the peripheral arteries in the human body.

It may further be understood that while in the above-embodiments, the cross sectional vessel lumen and the respective vessel diameter have been used as geometric parameters determined from the geometric model, other geometric parameters may likewise be derived.

Although in the above described embodiments the hemodynamic parameters derived based on the fluid dynamics model in the physiological model and the intravascular measurement data are related to the blood flow, it is to be understood that, likewise, other hemodynamic parameters may be derived, such as blood pressure, blood viscosity, vessel wall friction, or the like.

Further, it shall be understood that, also in the above described embodiments the fluid outflow from the vessel of interest through respective vessel branches has been assessed and modeled, the principles described above may likewise be used to assess and model the fluid inflow into the vessel of interest.

Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality.

A single unit or device may fulfill the functions of several items recited in the claims. The mere fact that certain measures are recited in mutually different dependent claims does not indicate that a combination of these measures cannot be used to advantage.

Procedures like the receiving of the at least one diagnostic image, the generating of a physiological model, the extraction of the geometric parameter values, the determining of the local reduction of the geometric parameter values, the predicting of the vessel branch et cetera performed by one or several units or devices can be performed by any other number of units or devices. These procedures in accordance with the invention can hereby be implemented as program code means of a computer program and/or as dedicated hardware.

A computer program may be stored/distributed on a suitable medium, such as an optical storage medium or a solid-state medium, supplied together with or as part of other hardware, but may also be distributed in other forms, such as via the Internet or other wired or wireless telecommunication systems.

Any reference signs in the claims should not be construed as limiting the scope.

The invention relates to an apparatus for assessing a patient's vasculature, comprising an input unit configured to receive at least one diagnostic image of the vasculature, a modeling unit configured to generate, on the basis of the at least one diagnostic image, a physiological model comprising a geometric model of a vessel of interest in the vasculature, an extraction unit configured to extract, on the basis of the geometric model, a plurality of geometric parameter values for a geometric parameter of the vessel of interest at a plurality of positions along a longitudinal axis of the vessel of interest and an evaluation unit configured to determine, from the plurality of geometric parameter values at the plurality of positions, a local reduction of at least one geometric parameter value at at least one candidate position and to predict, at the at least one candidate position, at least one vessel branch of the vessel of interest.

By means of this apparatus an improved assessment of the patient's vasculature is enabled as the effects of fluid outflow from bifurcations in each vessel of interest are taken into consideration.

The invention claimed is:

1. An apparatus for assessing a patient's vasculature, the apparatus comprising:
   at least one processor coupled to memory, the at least one processor configured to:
      receive at least one diagnostic image of the vasculature;
      generate, based on the at least one diagnostic image, a physiological model comprising a geometric model of a first vessel in the vasculature;
      extract, based on the geometric model, a plurality of geometric parameter values for a geometric parameter of the first vessel at a plurality of positions along a longitudinal axis of the first vessel;
      based on the extracted plurality of geometric parameter values, identify one or more candidate positions, of the plurality of positions, having a local change of the geometric parameter;
      predict, based on the local change, a presence of a vessel branching from the first vessel at a candidate position of the one or more candidate positions; and
      output an indicator identifying the vessel branching in the geometric model of the first vessel.

2. The apparatus according to claim 1, wherein
   the at least one diagnostic image is obtained using X-ray angiography.

3. The apparatus according to claim 1, wherein:
   the physiological model further comprises a lumped parameter fluid dynamics model; and
   the at least one processor is further configured to adapt the lumped parameter fluid dynamics model based on the predicting of the vessel branching from the first vessel at the one or more candidate positions.

4. The apparatus according to claim 1, wherein the at least one processor is further configured to:
   segment the first vessel into one or more segments;
   determine, for each segment, at least one segmented geometric parameter value;
   apply a regression model on the at least one segmented geometric parameter value to calculate, for each segment, an averaged geometric parameter value; and
   predict the vessel branching from the first vessel by predicting at least one hemodynamic parameter at the one or more candidate positions on the basis of an averaged geometric parameter value of each segment.

5. The apparatus according to claim 4, wherein the predicting the at least one hemodynamic parameter comprises a predicting of a fluid outflow rate.

6. The apparatus according to claim 1,
   wherein the at least one processor is further configured to define a region of interest in the at least one diagnostic image based on the one or more candidate positions; and
   wherein the indicator that is output includes the region of interest.

7. The apparatus according to claim 6, wherein:
   the at least one processor is further configured to adapt the physiological model using the indicator of the region of interest.

8. The apparatus according to claim 6, further comprising:
   a display configured to,
      generate a first graphical representation of the at least one diagnostic image and a second graphical representation of the indicator of the region of interest; and
      jointly display the first graphical representation and the second graphical representation.

9. The apparatus according to claim 1, wherein the at least one processor is further configured to:
   receive intravascular measurement data; and
   predict, based on the physiological model and the intravascular measurement data, one or more hemodynamic index values at the plurality of positions along the longitudinal axis of the first vessel.

10. The apparatus according to claim 9, wherein the intravascular measurement data comprises at least one pressure gradient acquired in-situ for the first vessel.

11. The apparatus according to claim 9, wherein the one or more hemodynamic index values predicted at the plurality of positions along the longitudinal axis of the first vessel comprises at least one of a volumetric flow rate or a blood flow velocity.

12. The apparatus of claim 1, wherein a first geometric parameter value of the plurality of geometric parameter values comprises at least one of:
   a value for a vessel diameter,
   a local average vessel diameter, or
   an estimated healthy vessel diameter that virtually removes an effect of a disease on the vessel diameter at the plurality of positions.

13. A method for assessing a patient's vasculature, the method comprising the steps of:
   receiving at least one diagnostic image of the vasculature;
   generating, based on the at least one diagnostic image, a physiological model comprising a geometric model of a first vessel in the vasculature;
   extracting, based on the geometric model, a plurality of geometric parameter values for a geometric parameter of the first vessel at a plurality of positions along a longitudinal axis of the first vessel;
   based on the extracted plurality of geometric parameter values, identifying one or more candidate positions, of the plurality of positions, having a local change of the geometric parameter;
   predicting, based on the local change, a presence of a vessel branching from the first vessel at a candidate position of the one or more candidate positions; and
   outputting an indicator identifying the vessel branching in the geometric model of the first vessel.

14. The method according to claim 13, further comprising:
   segmenting the first vessel into one or more segments;
   determining, for each segment, at least one segmented geometric parameter value;
   applying a regression model on the at least one segmented geometric parameter value to calculate, for each segment, an averaged geometric parameter value; and
   predicting the vessel branching from the first vessel by predicting at least one hemodynamic parameter at the one or more candidate positions on the basis of the averaged geometric parameter value of each segment.

15. A non-transitory computer-readable medium having stored thereon instructions which, when executed by a processor cause the processor to:
   receive at least one diagnostic image of the vasculature;
   generate, based on the at least one diagnostic image, a physiological model comprising a geometric model of a first vessel in the vasculature;
   extract, based on the geometric model, a plurality of geometric parameter values for a geometric parameter of the first vessel at a plurality of positions along a longitudinal axis of the first vessel; and based on the extracted plurality of geometric parameter values, identify one or more candidate positions, of the plurality of positions, having a local change of the geometric parameter;

predict, based on the local change, a presence of a vessel branching from the first vessel at a candidate position of the one or more candidate positions; and output an indicator identifying the vessel branching in the geometric model of the first vessel.

* * * * *